United States Patent [19]
De Marinis et al.

[11] 3,960,852
[45] June 1, 1976

[54] SUBSTITUTED SULFONYLACETAMIDO CEPHALOSPORINS

[75] Inventors: Robert M. De Marinis, King of Prussia; John R. E. Hoover, Glenside, both of Pa.

[73] Assignee: Smithkline Corporation, Philadelphia, Pa.

[22] Filed: Dec. 3, 1974

[21] Appl. No.: 529,162

Related U.S. Application Data

[62] Division of Ser. No. 249,858, May 3, 1972, Pat. No. 3,865,819.

[52] U.S. Cl............................................ 260/243 C
[51] Int. Cl.$^2$...................................... C07D 501/50
[58] Field of Search ............................... 260/243 C

[56] References Cited
UNITED STATES PATENTS
3,382,238  5/1968  Dolfini........................... 260/239.1

OTHER PUBLICATIONS

Lewis et al., Antimicrobial Agents & Chemotherapy (1968), pp. 109–114 (1969).
Terao et al., Chem. Abstacts, vol. 79, 18,739p (1973).
Soma et al., Chemical Abstracts, vol. 79, 105,305n (1973).

*Primary Examiner*—Alton D. Rollins
*Assistant Examiner*—Rivers, Diana G.
*Attorney, Agent, or Firm*—Stuart R. Suter; William H. Edgerton; Alan D. Lourie

[57] ABSTRACT

Cephalosporin compounds having various substituted sulfonylacetamido groups at position 7 have been prepared and have antibacterial activity.

5 Claims, No Drawings

SUBSTITUTED SULFONYLACETAMIDO CEPHALOSPORINS

This is a division of application Ser. No. 249,858 filed May 3, 1972, now U.S. Pat. No. 3,865,819.

This invention relates to cephalosporin compounds which have antibacterial activity, in particular, compounds having a substituted sulfonylacetamido substituent at position 7 of the cephem nucleus.

The compounds of this invention are represented by the following structure.

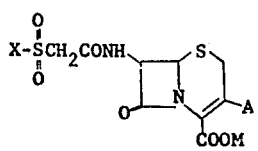

where:

X is lower alkyl of $C_1$–$C_6$; phenyl, unsubstituted or substituted with nitro, amino, dialkylamino, each alkyl having $C_1$–$C_4$, hydroxy, alkoxy ($C_1$–$C_4$), or halogen; $CF_3$; $NH_2$; or mono or dialkylamino, each alkyl of $C_1$–$C_4$;

A is hydrogen, methyl, acetoxymethyl, pyridiniummethyl, $CH_2$S-Het, $CH_2$SR, or $CH_2$OR;

Het is a 5 or 6-membered heterocyclic ring containing one to four atoms selected from the group consisting of N, O and S, unsubstituted or substituted with from one to two groups selected from lower alkyl, cycloalkyl or alkenyl, each having one to four carbon atoms; lower alkoxy or alkoxyalkyl, each alkoxy or alkyl having one to four carbon atoms; hydroxy; $CF_3$; NHR; $NR_2$; SR; or halogen;

R is hydrogen or lower alkyl ($C_1$–$C_4$); and

M is hydrogen, alkali metal cation, nontoxic ammonium cation, or when A is pyridiniummethyl an anionic charge.

Cephalosporins with a wide variety of acyl groups at position 7 are known in the prior art including substituted sulfinylalkanoyl groups. The present invention relates to substituted sulfonylacetamidocephalosporins, having a doubled oxidized sulfur atom.

Preferred compounds are those where A is $CH_2$S-Het and in particular where Het is tetrazolyl, 1,3,4-thiadiazolyl, 1,3,4-oxadiazolyl, 1,2,4-triazolyl, 1,2,3-triazolyl and the substituted derivatives thereof. Also preferred are compounds where X is methyl, ethyl, propyl, trifluoromethyl, phenyl, amino and dimethylamino.

The compounds of this invention are prepared by acylation of a 7-aminocephalosporanic acid with the appropriately substituted sulfonylacetic acid. The carboxyl group is activated prior or during the acylation reaction by one of the methods well known in the art. These include the mixed anhydride, acid halide and activated ester methods and the use of a coupling reagent such as dicyclohexylcarbodiimide.

The alkyl and arylsulfonylacetic acids are prepared by oxidation of the appropriate substituted mercaptoacetic acid with an oxidizing agent; for example, methylmercaptoacetic acid is oxidized with m-chloroperbenzoic acid to give methylsulfonylacetic acid. Alternatively the substituted mercaptoacetic acid can be converted to an activated ester, such as the N-hydroxysuccinimide ester or the 2,4-dinitrophenyl ester, and then oxidized to the activated sulfonylacetate. Aminosulfonylacetic acids (i.e., $XSO_2CH_2COOH$ where X is amino or dialkylamino) are prepared from commercially available chlorosulfonylacetyl chloride by known methods (*J. Amer. Chem. Soc.*, 81, 5655 (1959); British Pat. No. 1,067,965).

The 7-aminocephalosporins where A is $CH_2$S-Het are prepared by known methods from 7-aminocephalosporanic acid (7-ACA) and the appropriate heterocyclic mercaptan compound. The compounds where A is pyridiniummethyl are prepared by acylation of 7ACA and then reaction with pyridine by known procedures. The compounds where A is hydrogen, methyl, alkylthiomethyl, or alkoxymethyl are prepared from materials known in the art, readily prepared by known methods or described herein.

The compounds of this invention have broad-spectrum antibacterial activity with minimum inhibitory concentrations (MIC) ranging from 0.1 to >200 ug/ml. Table 1 shows MIC's for a variety of compounds within the scope of this invention against various Gram-positive and Gram-negative bacteria.

TABLE 1

| Cmpd. No.* | S. aureus HH 127 | S. aureus SK 23390 | S. villaluz | Strep. pyog. C 203 | Strep. faecalis HH 34358 | E. coli SK 12140 | E. coli HH 33779 | Kleb. pneumo. SK 4200 | Kleb. pneumo. SK 1200 | Pseudo. SP. HH 63 | Salmonella ATCC 12176 | Shigella HH 112 | Entero aerog. ATCH 13048 | Serra. marc. ATCC 13880 | Entero. cloaca PaSL 969 |
|---|---|---|---|---|---|---|---|---|---|---|---|---|---|---|---|
| | | | | | | | MIC (µg/ml) | | | | | | | | |
| 54293 | 3.1 | 1.6 | | 0.4 | 200 | 12.5 | 25 | 12.5 | 12.5 | >200 | 12.5 | 25 | >200 | | >200 |
| 55848 | 1.6 | 1.6 | | 0.2 | 50 | 12.5 | 25 | 3.1 | 6.3 | >200 | 3.1 | 12.5 | >200 | | >200 |
| 57286 | 3.1 | 1.6 | | 0.2 | 100 | 3.1 | 12.5 | 1.6 | 3.1 | >200 | 3.1 | 3.1 | >200 | >200 | >200 |
| 57359 | 1.6 | 0.8 | | 0.2 | 50 | 50 | 100 | 12.5 | 6.3 | >200 | 12.5 | 25 | >200 | >200 | >200 |
| 57360 | 0.8 | 0.4 | | 0.1 | 25 | 25 | 100 | 25 | 12.5 | >200 | 25 | 25 | >200 | >200 | >200 |
| 59345 | 0.8 | 0.8 | 25 | 0.1 | 100 | 100 | 100 | 50 | 100 | >200 | 50 | 50 | >200 | >200 | >200 |
| 59393 | 1.6 | 1.6 | 25 | 0.1 | 50 | 50 | 50 | 25 | 25 | >200 | 12.5 | 25 | 200 | >200 | 100 |
| 59454 | 25 | 25 | >200 | 0.4 | >200 | >200 | >200 | >200 | >200 | >200 | >200 | >200 | >200 | >200 | >200 |
| 59586 | 1.6 | 0.8 | 100 | 0.2 | 100 | 6.3 | 25 | 3.1 | 3.1 | >200 | 1.6 | 12.5 | 200 | >200 | >200 |
| 59623 | 0.8 | 0.8 | 100 | 0.1 | 100 | 25 | 50 | 6.3 | 6.3 | >200 | 3.1 | 25 | 200 | >200 | |
| 59641 | 0.4 | 0.4 | 100 | 0.1 | 25 | 3.1 | 12.5 | 1.6 | 1.6 | >200 | 1.6 | 6.3 | 100 | >200 | |
| 59758 | 3.1 | 1.6 | 50 | 0.1 | 200 | 6.3 | 12.5 | 6.3 | 6.3 | >200 | 3.1 | 0.1 | >200 | >200 | |
| 59857 | 1.6 | 1.6 | 25 | 0.2 | 100 | 25 | 50 | 6.3 | 6.3 | >200 | 3.1 | 25 | >200 | >200 | |

*See Table 2 for structures

TABLE 2

| Compound No. | X | A |
|---|---|---|
| 54293 | methyl | acetoxymethyl |
| 55848 | methyl | 5-methyl-1,3,4-thiadiazol-2-ylthiomethyl |
| 57286 | methyl | 1-methyltetrazol-5-ylthiomethyl |
| 57359 | phenyl | acetoxymethyl |
| 57360 | phenyl | 5-methyl-1,3,4-thiadiazol-2- |

TABLE 2-continued

| Compound No. | X | A |
|---|---|---|
| 59345 | methyl | ylthiomethyl pyridiniummethyl |
| 59393 | amino | acetoxymethyl |
| 59454 | methyl | methyl |
| 59586 | methyl | 5-methyl-1,2,4-triazol-3-ylthiomethyl |
| 59623 | ethyl | acetoxymethyl |
| 59641 | ethyl | 5-methyl-1,3,4-thiadiazol-2-ylthiomethyl |
| 59758 | methyl | 4-methyl-1,2,4-triazol-3-yl-thiomethyl |
| 59857 | methyl | 4-methyl-5-oxo-1,2,4-triazol-3-ylthiomethyl |

These compounds are formulated and administered in the same manner as other cephalosporins with the dose depending on the subject and the infection being treated.

The following examples illustrate the invention but are not to be construed as limiting the scope thereof.

EXAMPLE 1

7-Methylsulfonylacetamidocephalosporanic acid

Dicyclohexylcarbodiimide (20.6 g, 0.1 mol) was added to a solution of methylmercaptoacetic acid (10.7 g, 0.10 mol) and N-hydroxysuccinimide (11.5 g, 0.1 mol) in dry tetrahydrofuran (100 ml). The mixture was stirred in an ice bath for 1 hour and then allowed to stand overnight. The precipitate was collected and the filtrate was evaporated to give the crude product which was recrystallized from carbon tetrachloride.

The above activated ester (4.06 g, 0.02 mol) was dissolved in chloroform (40 ml) and the solution was cooled to 0°. To this was added over a 15 minute period a solution of m-chloroperbenzoic acid (8.1 g, 0.04 mol) in ether (50 ml). The reaction is stirred 1 hour in an ice bath and 3 days at room temperature. The precipitated product was collected and was recrystallized from acetone to give the methylsulfonylacetate ester.

To a suspension of 7-ACA (1.64 g, 0.06 mol) in dry dimethylformamide (20 ml) was added sufficient triethylamine to effect solution. The above ester (1.4 g, 0.06 mol) was added to the solution at room temperature with stirring. After 1.25 hours the reaction was poured into ice water and the aqueous mixture was acidified to pH2 and extracted with ethyl acetate. The extracts were dried and concentrated to a volume of about 20 ml. An equal volume of ether was added followed by sodium 2-ethylhexanoate and then more ether (100 ml.). The precipitate was collected, washed with ether, and dried to yield the title compound as its sodium salt. The free acid is obtained by acidification of an aqueous solution of the sodium salt.

EXAMPLE 2

7-Methylsulfonylacetamido-3-(1-methyltetrazol-5-ylthiomethyl)-3-cephem-4-carboxylic acid To a suspension of 7-amino-3-(1-methyltetrazol-5-ylthiomethyl)-3-cephem-4-carboxylic acid (1.09 g, 3 mmol) in dimethylformamide (25 ml) was added triethylamine until all the solid was dissolved. The activated methylsulfonylacetate ester from Example 1 (0.705 g, mmol) was added to the solution in one portion. The reaction solution was stirred at room temperature for 5 hours and then was added dropwise to ether (200 ml). The gummy precipitate was stirred with filter aid and filtered. The filter cake was washed with ether, and then stirred with acetonitrile (50 ml) and filtered again. The filtrate was evaporated to a gummy residue which was dissolved in water (40 ml). The aqueous phase was extracted with ethyl acetate (40 ml), acidified to pH 2, and reextracted with ethyl acetate. The organic extracts of the acidic solution were washed with water, dried and concentrated to a volume of about 50 ml. Sodium 2-ethylhexanoate in isopropanol was added to precipitate the sodium salt of the title compound. The free acid is obtained from the sodium salt by standard methods.

EXAMPLE 3

7-Methylsulfonylacetamido-3-(2-methyl-1,3,4-thiadiazol-5-ylthiomethyl)-3-cephem-4-carboxylic acid Triethylamine was added to a suspension of 7-amino-3-(2-methyl-1,3,4-thiadiazol-5-ylthiomethyl)-3-cephem-4-carboxylic acid (1.72 g, 5 mmol) in dimethylformamide (25 ml) until a slight cloudiness remained. To this was added the activated sulfonyl ester from Example 1 (1.18 g, 5 mmol) and the reaction was stirred at room temperature for 2 hours. The resultant was poured into ice water (150 ml) and the aqueous solution was extracted with ethyl acetate. The aqueous phase was acidified with 3N HCl to pH 2 and extracted with ethyl acetate. The combined extracts were washed with water, dried and concentrated to a volume of 50 ml. Sodium 2-ethylhexanoate was added and then ether (200 ml). The precipitated sodium salt was collected, washed with ether and dried. By standard methods, the free acid is obtained from the sodium salt.

EXAMPLE 4

7-Phenylsulfonylacetamido-3-(2-methyl-1,3,4-thiadiazol-5-ylthiomethyl)-3-cephem-4-carboxylic acid When phenylmercaptoacetic acid was reacted with N-hydroxysuccinimide and then m-chloroperbenzoic acid according to the procedure in Example 1, N-hydroxysuccinimidyl phenylsulfonylacetate was obtained.

7-Amino-3-(2-methyl-1,3,4-thiadiazol-5-ylthiomethyl)-3-cephem-4-carboxylic acid (1.38 g, 0.04 mol) was suspended in dimethylformamide (25 ml) and triethylamine was added until solution was effected. The above ester (1.1 g, 0.04 mol) was added and the reaction was stirred for 2 hours at room temperature. The solution was added dropwise to ether (200 ml). The suspension was filtered through filter aid and the filter cake was washed with ether. The product and filter aid were stirred with water (50 ml) for 20 minutes and refiltered. The aqueous filtrate was extracted with ethyl acetate (which was discarded) and then acidified to pH 1 with 3N HCl and reextracted with ethyl acetate. The extracts were washed with water, dried, and sodium 2-ethylhexanoate was added. The sodium salt was collected and dried. An aqueous solution of the sodium salt is adjusted to pH 2 and the free acid is collected.

EXAMPLE 5

7-Phenylsulfonylacetamidocephalosporanic acid

When the activated phenylsulfonylacetate of Example 4 was reacted with 7-ACA according to the same procedure as Example 4, the title compound was obtained.

EXAMPLE 6

7-Trifluoromethylsulfonylacetamido-3-(2-methyl-1,3,4-thiadiazol-5-ylthiomethyl)-3-cephem-4-carboxylic acid Trifluoromethylmethylsulfone (1.48 g, 0.01 mol) [W. E. Truce, et al., *J. Amer. Chem. Soc.*, 74, 3594 (1952)] was dissolved in dry ether (50 ml) and the solution was cooled to −40°. A 2 molar solution of n-butyl lithium (7.5 ml, 0.015 mol) was added; the reaction was warmed to ca. 15°, stirred for 30 minutes, and then poured over crushed $CO_2$ with stirring. When the mixture reached room temperature it was shaken with water (75 ml); the aqueous phase was separated, acidified to pH 1.5, and extracted with ether. The extracts were dried and evaporated to give an oil which crystallized on standing. The trifluoromethylsulfonylacetic acid was recrystallized from carbon tetrachloride.

Using the procedure in Example 1 trifluoromethylsulfonylacetic acid is esterified with N-hydroxysuccinimide and then is reacted with 7-amino-3-(2-methyl-1,3,4-thiadiazol-5-ylthiomethyl)-3-cephem-4-carboxylic acid using the procedure of Example 3 to give the title compound.

EXAMPLE 7

7-Trifluoromethylsulfonylacetamidocephalosporanic acid

The reaction of the activated ester of trifluoromethylsulfonylacetic acid from Example 6 with 7-ACA according to the procedure of Example 1 gives the title compound.

EXAMPLE 8

7-Aminosulfonylacetamidocephalosporanic acid

Dicyclohexylcarbodiimide (1 g, 5 mmol) was added to a solution of 7-ACA t-butyl ester (1.65 g, 5 mmol) and aminosulfonylacetic acid (0.7 g, 5 mmol) (British Pat. No. 1,067,965) in dry tetrahydrofuran (15 ml). The solution was stirred overnight at room temperature, filtered and the precipitate was washed with tetrahydrofuran. The filtrate and washings were combined and evaporated to a gum. The gum was reacted with trifluoroacetic acid (5 ml) for 15 minutes at room temperature and then the reaction solution was added dropwise to ether (150 ml). The precipitate was filtered, washed with ether, then stirred with ethyl acetate and filtered. The filtrate was treated with sodium 2-ethylhexanoate in isopropanol. The precipitated sodium salt was collected, washed with ether and acetonitrile and dried. The sodium salt is converted to the free acid by standard methods.

EXAMPLE 9

7-Aminosulfonylacetamido-3-(2-methyl-1,3,4-thiadiazol-5-ylthiomethyl)-3-cephem-4-carboxylic acid Using the procedure of Example 3, 7-amino-3-(2-methyl-1,3,4-thiadiazol-5-ylthiomethyl)-3-cephem-4carboxylic acid is reacted with N-hydroxysuccinimidyl aminosulfonylacetate (prepared in a similar manner as set forth in Example 1 from aminosulfonylacetic acid and N-hydroxysuccinimide) to give the desired product.

EXAMPLE 10

When an equivalent amount of a 7-amino-3-heterocyclicthiomethyl-3-cephem-4-carboxylic acid listed below is substituted in Example 2 for 7-amino-3-(1-methyltetrazol-5-ylthiomethyl)-3-cephem-4-carboxylic acid, the appropriate 7-methylsulfonylacetamido-3-heterocyclicthiomethyl-3-cephem-4-carboxylic acid is obtained.

7-Amino-3-(1,3,4-thiadiazol-2-ylthiomethyl)-3-cephem-4-carboxylic acid
7-Amino-3-(5-trifluoromethyl-1,3,4-thiadiazol-2-ylthiomethyl)-3-cephem-4-carboxylic acid
7-Amino-3-(5-ethyl-1,3,4-thiadiazol-2-ylthiomethyl)-3-cephem-4-carboxylic acid
7-Amino-3-(5-n-butyl-1,3,4-thiadiazol-2-ylthiomethyl)-3-cephem-4-carboxylic acid
7-Amino-3-(5-dimethylamino-1,3,4-thiadiazol-2-ylthiomethyl)-3-cephem-4-carboxylic acid
7-Amino-3-(5-mercapto-1,3,4-thiadiazol-3-ylthiomethyl)-cephem-4-carboxylic acid
7-Amino-3-(3-methylthio-1,2,4-thiadiazol-5-ylthiomethyl)-3-cephem-4-carboxylic acid
7-Amino-3-(3-methyl-1,2,4-thiadiazol-5-ylthiomethyl)-3-cephem-4-carboxylic acid
7-Amino-3-(tetrazol-5-ylthiomethyl)-3-cephem-4-carboxylic acid
7-Amino-3-(1,2,4-triazol-3-ylthiomethyl)-3-cephem-4-carboxylic acid
7-Amino-3-(5-methyl-1,2,4-triazol-3-ylthiomethyl)-3-cephem-4-carboxylic acid
7-Amino-3-(4-methyl-1,2,4-triazol-3-ylthiomethyl)-3-cephem-4-carboxylic acid
7-Amino-3-(4,5-dimethyl-1,2,4-triazol-3-ylthiomethyl)-3-cephem-4-carboxylic acid
7-Amino-3-(2,5-dimethyl-1,2,4-triazol-3-ylthiomethyl)-3-cephem-4-carboxylic acid
7-Amino-3-(4-methyl-5-trifluoromethyl-1,2,4-triazol-3-ylthiomethyl)-3-cephem-4-carboxylic acid
7-Amino-3-(5-ethyl-1,2,4-triazol-3-ylthiomethyl)-3-cephem-4-carboxylic acid
7-Amino-3-(4-ethyl-1,2,4-triazol-3-ylthiomethyl)-3-cephem-4-carboxylic acid
7-Amino-3-(2-methyl-1,2,4-triazol-3-ylthiomethyl)-3-cephem-4-carboxylic acid
7-Amino-3-(2-ethyl-1,2,4-triazol-3-ylthiomethyl)-3-cephem-4-carboxylic acid
7-Amino-3-(4-allyl-1,2,4-triazol-3-ylthiomethyl)-3-cephem-4-carboxylic acid
7-Amino-3-(5-methoxymethyl-1,2,4-triazol-3-ylthiomethyl)-3-cephem-4-carboxylic acid
7-Amino-3-(5-cyclopropyl-1,2,4-triazol-3-ylthiomethyl)-3-cephem-4-carboxylic acid
7-Amino-3-(5-bromo-1,2,4-triazol-3-ylthiomethyl)-3-cephem-4-carboxylic acid
7-Amino-3-(5-hydroxy-1,2,4-triazol-3-ylthiomethyl)-3-cephem-4-carboxylic acid
7-Amino-3-(5-hydroxy-4-methyl-1,2,4-triazol-3-ylthiomethyl)-3-cephem-4-carboxylic acid
7-Amino-3-(5-hydroxy-4-ethyl-1,2,4-triazol-3-ylthiomethyl)-3-cephem-4-carboxylic acid
7-Amino-3-(1,2,3-triazol-5-ylthiomethyl)-3-cephem-4-carboxylic acid
7-Amino-3-(1,3,4-oxadiazol-2-ylthiomethyl)-3-cephem-4-carboxylic acid
7-Amino-3-(5-methyl-1,3,4-oxadiazol-2-ylthiomethyl)-3-cephem-4-carboxylic acid 7-Amino-3-(4-pyrimidylthiomethyl)-3-cephem-4-carboxylic acid
7-Amino-3-(2-pyrazinylthiomethyl)-3-cephem-4-carboxylic acid
7-Amino-3-(3-pyridylthiomethyl)-3-cephem-4-carboxylic acid
7-Amino-3-(4-pyridylthiomethyl)-3-cephem-4-carboxylic acid

EXAMPLE 11

The reaction of 7-amino-3-(1-methyltetrazol-5-ylthiomethyl)-3-cephem-4-carboxylic acid or a 7-amino-3-heterocyclicthiomethyl-3-cephem-4-carboxylic acid enumerated in Example 10 with activated phenylsulfonylacetate ester according to the procedure of Example 4 gives the appropriate 7-phenylsulfonylacetamido-3-heterocyclicthiomethyl-3-cephem-4-carboxylic acid.

EXAMPLE 12

When the procedure of Example 6 is followed using 7-amino-3-(1-methyltetrazol-5-ylthiomethyl)-3-cephem-4-carboxylic acid or a 7-amino-3-heterocyclicthiomethylcephalosporin listed in Example 10, the corresponding 7-trifluoromethylsulfonylacetamido-3-heterocyclicthiomethyl-3-cephem-4-carboxylic acid is obtained.

EXAMPLE 13

Substitution of 7-amino-3-(1-methyltetrazol-5-ylthiomethyl)-3-cephem-4-carboxylic acid or a cephalosporin compound listed in Example 10 in the procedure of Example 9 gives the appropriate 7-aminosulfonylacetamido-3-heterocyclicthiomethyl-3-cephem-4-carboxylic acid product.

EXAMPLE 14

7-Methylsulfonylacetamido-3-(1-pyridiniummethyl)-3-cephem-4-carboxylic acid

To a solution of 7-methylsulfonylacetamidocephalosporanic acid sodium salt (1.75 g 4.0 mmol) in water (2 ml) was added potassium thiocyanate (7.87 g, 0.081 mol), water (2 ml) and pyridine (0.44 ml). The reaction was heated at 65°–70° for 7 hours and then was cooled. The solution was diluted with water (75 ml) and the aqueous solution was chromatographed on a column of cross-linked polystyrene polymer (125 g of Amberlite XAD-2). The inorganic salts were eluted with water and then the product was eluted with 95% ethanol. The ethanol fractions were evaporated to give the crude product which was dissolved in water, filtered and lyophilized.

EXAMPLE 15

When trifluoromethylsulfonylacetamidocephalosporanic acid, aminosulfonylacetamidocephalosporanic acid, or phenylsulfonylacetamidocephalosporanic acid is substituted for methylsulfonylacetamidocephalosporanic acid in Example 14 the corresponding 3-(1-pyridiniummethyl)cephalosporin is obtained.

EXAMPLE 16

7-(N,N-Dimethylaminosulfonylacetamido)-3-(2-methyl-1,3,4-thiadiazol-5-yl)-3-cephem-4-carboxylic acid N,N-Dimethylaminosulfonylacetic acid is prepared in an analogous method as aminosulfonylacetic acid and then is reacted with 7-amino-3-(2-methyl-1,3,4-thiadiazol-5-ylthiomethyl)-3-cephem-4-carboxylic acid according to the procedure of Example 9 to give the title compound.

EXAMPLE 17

When 7-amino-3-(1-methyltetrazol-5-ylthiomethyl)-3-cephem-4-carboxylic acid or a 7-amino-3-heterocyclic cephalosporin enumerated in Example 10 is reacted with N,N-dimethylaminosulfonylacetic acid by the procedure of Example 16 the corresponding 7-(N,N-dimethylaminosulfonylacetamido)-3-heterocyclicthiomethyl-3-cephem-4-carboxylic acid is obtained.

EXAMPLE 18

The reaction of N,N-dimethylaminosulfonylacetic acid with 7-ACA t-butyl ester according to the procedure of Example 8 gives 7-(N,N-dimethylaminosulfonylacetamido) cephalosporanic acid.

When the above product is reacted with pyridine using the procedure of Example 14, 7-(N,N-dimethylaminosulfonylacetamido)-3-(1-pyridiniummethyl)-3-cephem-4-carboxylic acid is obtained.

EXAMPLE 19

7-Methylsulfonylacetamido-3-methyl-3-cephem-4-carboxylic acid

7-Amino-3-methyl-3-cephem-4-carboxylic acid (7-ADCA) (2.14 g, 0.01 mol) was suspended in dry dimethylformamide (30 ml) and 1,5-diazobicyclo[4.3.0]non-5-ene was added until only a slight cloudiness remained. The activated ester from Example 1 (2.35 g, 0.01 mol) was added and the reaction was stirred for 2.5 hours at room temperature. The solution was filtered into ether (300 ml) and then the filtrate was filtered through filter aid. The filter was stirred with water (50 ml) and refiltered. The filtrate was acidified to pH 1.5 with 3N HCl and extracted with ethyl acetate. The organic extracts were washed with water, dried, and concentrated to ca. 50 ml. Sodium 2-ethylhexanoate was added and the precipitated sodium salt was collected, washed with ethyl acetate and dried. The free acid is obtained from the sodium salt by standard methods.

EXAMPLE 20

When the activated esters of phenylsulfonylacetic acid, trifluoromethylsulfonylacetic acid, aminosulfonylacetic acid, or N,N-dimethylaminosulfonylacetic acid are reacted with 7-ADCA according to the procedure in Example 19 the corresponding 7-sulfonylacetamido-3-methyl-3-cephem-4-carboxylic acid is obtained.

EXAMPLE 21

7-Ethylsulfonylacetamidocephalosporanic acid

N-hydroxysuccinimidyl ethylsulfonylacetate was prepared from ethylmercaptoacetic acid according to the procedure of Example 1. To a suspension of 7-ACA (2.18 g, 8 mmol) in dry dimethylformamide (50 ml) was added triethylamine until solution was effected and then the activated ester (1.99 g, 8 mmol) was added in one portion. The resultant reaction mixture was stirred 1.5 hours at room temperature and then poured with stirring into ether (400 ml) which caused a gummy residue to precipitate. The mixture was filtered through Celite and the filter cake was stirred with water (100 ml) until the residue was dissolved. The aqueous solution was filtered, washed with ethyl acetate, covered with fresh ethyl acetate and acidified with 3N HCl to pH 2. The acidic solution was extracted with ethyl acetate. The combined extracts were washed with water, dried, and evaporated to give the title compound.

EXAMPLE 22

7-Ethylsulfonylacetamido-3-(2-methyl-1,3,5-thiadiazol-5-ylthiomethyl)-3-cephem-4-carboxylic acid Using the activated 7-ethylsulfonylacetate ester (1.99 g, 8 mmol) and 7-amino-3-(2-methyl-1,3,5-thiadiazol-5-ylthiomethyl)-3-cephem-4-carboxylic acid (2.75 g, 8 mmol) in the procedure of Example 21, the title compound was prepared.

EXAMPLE 23

When 7-amino-3-(1-methyltetrazol-5-ylthiomethyl)-3-cephem-4-carboxylic acid or any of the compounds enumerated in Example 10 are substituted for 7-ACA in the procedure of Example 21 the corresponding 7-ethylsulfonylacetamido-3-heterocyclicthiomethyl-3-cephem-4-carboxylic acid is obtained.

Similarly, 7-ethylsulfonylacetamido-3-methyl-3-cephem-4-carboxylic acid is obtained by acylating 7-ADCA using the procedure of Example 21.

EXAMPLE 24

Propylmercaptoacetic acid is converted into N-hydroxysuccinimidyl propylsulfonylacetate in the same manner as the methyl analog in Example 1. This ester is reacted with 7-ACA, 7-ADCA, 7-amino-3-(2-methyl-1,3,4-thiadiazol-5-ylthiomethyl)-3-cephem-4-carboxylic acid, 7-amino-3-(1-methyltetrazol-5-ylthiomethyl)-3-cephem-4-carboxylic acid, or any of the compounds enumerated in Example 10 according to the procedure of Example 21 to give the appropriate 7-propylsulfonylacetamidocephalosporin.

EXAMPLE 25

Acylation of 7-amino-3-methylthiomethyl-3-cephem-4-carboxylic acid (Belgian Pat. No. 743,754) with the activated esters of methylsulfonylacetic acid, ethylsulfonylacetic acid, or propylsulfonylacetic acid according to the procedure of Example 1 gives the corresponding 7-alkylsulfonylacetamido-3-methylthiomethyl-3-cephem-4-carboxylic acid. Using the procedure of Example 8 the above cephem nucleus is acylated with dimethylaminosulfonylacetic acid to give 7-dimethylaminosulfonylacetamido-3-methylthiomethyl-3-cephem-4-carboxylic acid.

EXAMPLE 26

Using the procedure of Example 1, 7-amino-3-methoxymethyl-3-cephem-4-carboxylic acid [*J. Med. Chem.*, 14, 113(1971)] is acylated with the activated ester of methylsulfonylacetic acid, ethylsulfonylacetic acid, or propylsulfonylacetic acid to give the corresponding 7-alkylsulfonylacetamido-3-methoxymethyl-3-cephem-4-carboxylic acid. The same cephem nucleus is acylated with dimethylaminosulfonylacetic acid by the procedure of Example 8 to give 7-dimethylaminosulfonylacetamido-3-methoxymethyl-3-cephem-4-carboxylic acid.

EXAMPLE 27

3-Formyl-7-(2-thienylacetamido)-2-cephem-4-carboxylic acid 7-(2-Thienylacetamido)cephalosporanic acid (45 g, 0.11 mol) was dissolved in dry pyridine (135 ml) by warming. This solution was cooled in an ice bath and acetic anhydride (13.5 ml) was added with stirring. After stirring 0.5 hour the reaction was stored in a refrigerator 18 hours during which time the mixture solidified. Ether was added to the mixture and the solid pyridine salt was collected and washed with ether. The salt was suspended in ethyl acetate (400 ml) with stirring and was collected again. The salt was then dissolved in a mixture of water (300 ml), ethyl acetate (400 ml) and 2N HCl (54 ml); the aqueous phase was saturated with NaCl and then was separated. The organic phase was washed with saturated NaCl solution, filtered through coarse filter paper three times, and evaporated to yield the $\Delta^2$-isomer (32.4 g).

The $\Delta^2$-isomer (32.4 g) was suspended in a mixture of acetone (60 ml) and water (300 ml) and 5% $Na_2CO_3$ solution was added until pH 10.5 was reached. The solution was allowed to stand two days during which time additional 5% $Na_2CO_3$ was added several times to maintain the solution at pH 10.5. The reaction was cooled in ice, layered with ethyl acetate and acidified with 6N $H_2SO_4$ to pH 1.8. The aqueous phase was saturated with NaCl and separated. The organic phase was washed with saturated NaCl solution, filtered through coarse filter paper and evaporated to give the product, the $\Delta^2$-3-hydroxymethyl compound (17.4 g).

A solution of the above product (17.4 g, 0.049 mol) in acetone (850 ml) was cooled to $-10°$ and then Jones reagent [chromic trioxide (26.72 g) dissolved in concentrated $H_2SO_4$ (23 ml) and then diluted to 100 ml with water] was added dropwise until the brown color persisted. Excess Jones reagent was decomposed with isopropanol, the green reaction mixture was filtered and the green precipitate was washed with acetone. The combined filtrate and washings were diluted with water (200 ml) and ethyl acetate (400 ml) and then saturated with NaCl. The organic phase was separated, washed with saturated NaCl solution and dried over $MgSO_4$. Evaporation of the solvent gave the crude product which was triturated with methanol to give the product as its methanoate (8.4 g). This product was dissolved in ethyl acetate (2000 ml) and then evaporated in vacuo to give the title compound (7.8 g).

EXAMPLE 28

Benzhydryl 3-formyl-7-(2-thienylacetamido)-2-cephem-4-carboxylate

A solution of diphenyldiazomethane (0.213 g, 1.1 mmol) in dry tetrahydrofuran (2 ml) was added dropwise with stirring to the 3-formyl-7-(2-thienylacetamido)-2-cephem-4-carboxylic acid (0.352 g., 1 mmol) in dry tetrahydrofuran (10 ml) at 40°. The reagent was allowed to completely react as noted by the color changes between each addition. The reaction was stirred at 40° for 2 hours after the addition was completed and then the solvent was removed in vacuo. The residual oil was dissolved in chloroform, washed with 5% $NaHCO_3$, dried over $MgSO_4$ and concentrated to half volume. The product was precipitated by the addition of hexane.

EXAMPLE 29

Benzhydryl-7-(2-thienylacetamido)-3-cephem-4-carboxylate

A mixture of the benzhydryl ester from Example 28 (2.5 g, 4.79 mmol), tris-(triphenylphosphine)chlororhodium (3.5 g. 4.79 mmol) and dry toluene (75 ml) was refluxed under nitrogen for 5.5 hours. The reaction mixture was cooled. The rhodium complex was removed by filtration and the filtrate was poured slowly into petroleum ether (250 ml) with stirring. The precipitated solid, which was a mixture of rhodium complex and product, was collected. The product was purified by chromatography on a silica gel column (250 g) using 99:0.5 chloroform:ethyl acetate as eluent. Fractions of 4.5 ml were collected; fractions 1–47 discarded, 48–66 contained bis-(triphenylphosphine)carbonylchlororhodium, and 67–198 contained the product. NMR data indicated the product after chromatography to be the $\Delta^3$ isomer instead of the $\Delta^2$ isomer. A decoupling experiment showed the 2-methylene group at 3.3 ppm. to be coupled with the 3-proton at 6.6 ppm.

EXAMPLE 30

Benzhydryl 7-amino-3-cephem-4-carboxylate

Benzhydryl 7-(2-thienylacetamido)-3-cephem-4-carboxylate (2.45 g. 5 mmol) was dissolved in calcium hydride dried benzene (130 ml) containing dry pyridine (0.59 g, 7.4 mmol). The solution was maintained at 0° and PCl$_5$ (1.54 g. 7.4 mmol.) was added with stirring. The reaction mixture was stirred under nitrogen at 0° for 3 hours and then the solvent was removed in vacuo. Anhydrous methanol (260 ml) was added to the residue and the resultant mixture was allowed to stand 2 hours. The methanol was removed in vacuo and the residue was treated with 20% aqueous tetrahydrofuran. After 15 minutes the tetrahydrofuran was removed in vacuo and the aqueous residue was adjusted to pH 7.5 and extracted with ethyl acetate. The extracts were washed with water, dried over MgSO$_4$ and evaporated to give the solid product which was triturated with chloroform-petroleum ether and dried under high vacuum.

EXAMPLE 31

7-Methylsulfonylacetamido-3-cephem-4-carboxylic acid

A solution of benzhydryl 7-amino-3-cephem-4-carboxylate (0.78 g, 2 mmol), methylsulfonylacetic acid (0.27 g, 2 mmol), and dicyclohexylcarbodiimide (0.4 g, 2 mmol) in dry tetrahydrofuran (15 ml) is stirred at room temperature overnight. The precipitate is collected and washed with tetrahydrofuran and the combined filtrate and washings are evaporated in vacuo. The residue is treated with a cold solution of trifluoroacetic acid (10 ml) and anisole (0.5 g) for 15 minutes and then concentrated in vacuo. The residue is dissolved in ethyl acetate and treated with 5% NaHCO$_3$. The aqueous phase is adjusted to pH 2 and the precipitated product is collected and dried.

EXAMPLE 32

When ethylsulfonylacetic acid, propylsulfonylacetic acid, trifluoromethylsulfonylacetic acid, phenylsulfonylacetic acid, aminosulfonylacetic acid, or N,N-dimethylaminosulfonylacetic acid is substituted for methylsulfonylacetic acid is the procedure of Example 31. The corresponding 7-sulfonylacetamido-3-cephem-4-carboxylic acid is obtained.

EXAMPLE 33

An injectable pharmaceutical composition is formed by adding sterile water or sterile saline solution (2 ml) to 500 mg of sodium 7-methylsulfonylacetamido-3-(1-methyltetrazol-5-ylthiomethyl)-3-cephem-4-carboxylate.

Pharmaceutical compositions of the other antibacterial compounds disclosed above may be formulated in a similar manner.

It is recognized that when the substituent on the heterocyclic group is hydroxy or mercapto that it is possible for the substituent to exist in another tautomeric form, i.e. the oxo or thiono form. The compounds may exist exclusively as one of the two tautomers or may be in equilibrium between the two; however, these are all included within the scope of this invention.

What we claim is:

1. A compound of the structure:

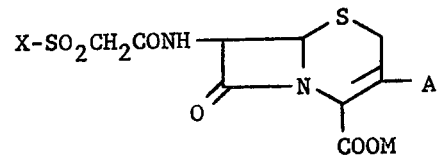

where:
X is CF$_3$;
A is CH$_2$S-Het;
Het is tetrazolyl, thiadiazolyl, triazolyl, oxadiazolyl, pyrimidyl, pyrazinyl or pyridyl, unsubstituted or substituted with one or two groups selected from the group consisting of lower alkyl, cycloalkyl, or alkenyl, each having one to four carbon atoms; lower alkoxy or alkoxyalkyl, each alkyl or alkoxy having one to four carbon atoms; hydroxy; CF$_3$; NHR; NR$_2$; SR; or bromine;
R is hydrogen or lower alkyl (C$_1$–C$_4$); and
M is hydrogen, alkali metal cation, or nontoxic ammonium cation.

2. A compound as claimed in claim 1 where Het is tetrazol-5-yl, 1,3,4-thiadiazol-5-yl, 1,2,4-triazol-3-yl, 1,2,3-triazol-5-yl or 1,3,4-oxadiazol-5-yl, each Het group being unsubstituted or substituted with hydroxy or one or two lower alkyl groups.

3. A compound as claimed in claim 2 being the coupound 7-trifluoromethylsulfonylacetamido-3-(1-methyltetrazol-5-ylthiomethyl)-3-cephem-4-carboxylic acid.

4. A compound as claimed in claim 2 being the compound 7-trifluoromethylsulfonylacetamido-3-(2-methyl-1,3,4-thiadiazol-5-ylthiomethyl)-3-cephem-4-carboxylic acid.

5. A compound as claimed in claim 2 being the compound 7-trifluoromethylsulfonylacetamido-3-(5-methyl-1,2,4-triazol-3-ylthiomethyl)-3-cephem-4-carboxylic acid.

* * * * *